US012788917B2

(12) United States Patent
Chen et al.

(10) Patent No.: US 12,788,917 B2
(45) Date of Patent: Nov. 10, 2026

(54) DISPOSABLE ANGLE-ADJUSTABLE VISUAL BRONCHIAL BLOCKER

(71) Applicant: YUANLONG (SHANGHAI) BIOTECHNOLOGY CO., LTD, Shanghai (CN)

(72) Inventors: Qiuxian Chen, Shanghai (CN); Changhai Yan, Shanghai (CN)

(73) Assignee: YUANLONG (SHANGHAI) BIOTECHNOLOGY CO., LTD, Shanghai (CN)

(*) Notice: Subject to any disclaimer, the term of this patent is extended or adjusted under 35 U.S.C. 154(b) by 333 days.

(21) Appl. No.: 18/730,767

(22) PCT Filed: Jan. 5, 2023

(86) PCT No.: PCT/CN2023/070591
§ 371 (c)(1),
(2) Date: Jul. 20, 2024

(87) PCT Pub. No.: WO2023/138385
PCT Pub. Date: Jul. 27, 2023

(65) Prior Publication Data

US 2025/0229045 A1 Jul. 17, 2025

(30) Foreign Application Priority Data

Jan. 21, 2022 (CN) ........................ 202210069245.4

(51) Int. Cl.
*A61M 16/04* (2006.01)
*A61B 1/00* (2006.01)
(Continued)

(52) U.S. Cl.
CPC ..... *A61M 16/0404* (2014.02); *A61B 1/00042* (2022.02); *A61B 1/00052* (2013.01);
(Continued)

(58) Field of Classification Search
CPC .......... A61B 17/12136; A61B 17/1204; A61B 17/12104; A61B 1/00042; A61B 1/00052; A61B 1/00117; A61B 1/00119; A61B 1/00128; A61B 1/00135; A61B 1/0052; A61B 1/0055; A61B 1/0057; A61B 1/05; A61B 1/0676; A61B 1/2676; A61M 2205/583; A61M 2205/587;
(Continued)

(56) References Cited

FOREIGN PATENT DOCUMENTS

CN 215537524 U * 1/2022

* cited by examiner

*Primary Examiner* — Ophelia A Hawthorne

(57) ABSTRACT

A disposable angle-adjustable visual bronchial blocker, including a bronchial blocking catheter which is divided into a stiff main catheter section (7) and a soft flexible section (3). An inflatable air bag (2) is arranged outside of the soft flexible section (3), and a camera assembly (1) is arranged at a front end of the soft flexible section (3). An interior of the bronchial blocking catheter includes a forward flexion control line (4), a backward extension control line (5), a ventilation lumen (6), an inflation line and a camera video line. A control handle (14) is arranged at a tail end of the bronchial blocking catheter, and an angle control disk (15) is arranged on a side face of the control handle (14). A front opening of the ventilation lumen (6) is formed in a front end face of the camera assembly (1).

7 Claims, 3 Drawing Sheets

(51) Int. Cl.

| | |
|---|---|
| ***A61B 1/005*** | (2006.01) |
| ***A61B 1/05*** | (2006.01) |
| ***A61B 1/06*** | (2006.01) |
| ***A61B 1/267*** | (2006.01) |
| ***A61M 16/20*** | (2006.01) |

(52) U.S. Cl.
CPC ...... *A61B 1/00117* (2013.01); *A61B 1/00119* (2013.01); *A61B 1/00128* (2013.01); *A61B 1/00135* (2013.01); *A61B 1/0052* (2013.01); *A61B 1/0055* (2013.01); *A61B 1/0057* (2013.01); *A61B 1/05* (2013.01); *A61B 1/0676* (2013.01); *A61B 1/2676* (2013.01); *A61M 16/0418* (2014.02); *A61M 16/0434* (2013.01); *A61M 16/209* (2014.02); *A61M 2202/0007* (2013.01); *A61M 2202/0208* (2013.01); *A61M 2205/0216* (2013.01); *A61M 2205/502* (2013.01); *A61M 2205/587* (2013.01)

(58) Field of Classification Search
CPC .... A61M 2205/502; A61M 2205/0216; A61M 16/209; A61M 16/0434; A61M 16/0418; A61M 16/0404
See application file for complete search history.

DISPOSABLE ANGLE-ADJUSTABLE VISUAL BRONCHIAL BLOCKER

CROSS-REFERENCE TO RELATED APPLICATION

This patent application is a national stage application of International Patent Application No. PCT/CN2023/070591, filed on Jan. 5, 2023, which claims priority of Chinese Patent Application No. 202210069245.4, filed on Jan. 21, 2022, both of which are incorporated by reference in their entirety.

TECHNICAL FIELD

The present disclosure belongs to the technical field of medical devices, and in particular to a disposable angle-adjustable visual bronchial blocker.

BACKGROUND

Intrathoracic surgery often requires single-lung ventilation, which specifically means that a bronchus on an affected side is isolated to collapse a lung on the affected side, a lung on another side is mechanically ventilated to maintain oxygenation during operation, and such a technique of isolating unilateral lung is also called pulmonary isolation. Pulmonary isolation usually adopts double-lumen endotracheal intubation, and trachea and bronchial cuffs are inflated to isolate the left and right bronchi, respectively. A main disadvantage of double-lumen endotracheal tube is that a tube is hick and hard, leading to common postoperative sore throat and glottis and airway injury. Pulmonary isolation can also be achieved using single-lumen endotracheal intubation combined with a bronchial blocker, that is, the bronchial blocker enters the bronchus through endotracheal intubation to block the trachea on this side through bronchial cuff. At present, there are two types of bronchial blockers, one type is a stiff bronchial blocker, which can be adjusted in a direction from side to side to enter the bronchus on a certain side after being placed in the tracheal catheter, and the other type is a soft bronchial blocker, the front end of which needs to be sleeved on a fiberoptic bronchoscope for guidance. However, no matter which bronchial blocker, the fiberoptic bronchoscope is required to confirm the position or guide the position. However, disinfection of the fiberoptic bronchoscope is complicated, and the efficiency is often difficult to meet clinical operation, and imperfect disinfection is easy to cause cross infection. Therefore, there is a need to design a disposable angle-adjustable visual bronchial blocker to solve the above problem.

SUMMARY

A technical problem to be solved by the present disclosure is to provide a disposable angle-adjustable visual bronchial blocker, which can improve clinical operation efficiency without using a fiberoptic bronchoscope for guidance.

A technical solution adopted by the present disclosure to solve the technical problem thereof is to provide a disposable angle-adjustable visual bronchial blocker, including a bronchial blocking catheter. The bronchial blocking catheter includes a stiff main catheter section and a soft flexible section. An inflatable air bag is arranged at an outer side of the flexible section, and a camera assembly is arranged at a front end of the flexible section. An interior of the bronchial blocking catheter includes a forward flexion control line, a backward extension control line, a ventilation lumen, an inflation line and a camera video line, and the forward flexion control line, the backward extension control line, the ventilation lumen, the inflation line and the camera video line are arranged in parallel in a direction of the bronchial blocking catheter. A control handle is arranged at a tail end of the bronchial blocking catheter, and an angle control disk for controlling a degree of bending of the soft flexible section is arranged on a side face of the control handle. A front opening of the ventilation lumen is formed in a front end face of the camera assembly.

Further, an interior of the angle control disk includes a base, a top cover, a hollow rotating shaft, a forward flexion control line fulcrum, a backward extension control line fulcrum and a control line fixer. The base is fixedly connected to the control handle, the hollow rotating shaft and the angle control disk are concentric, an end of the hollow rotating shaft is rotatably connected to the control handle, and another end of the hollow rotating shaft is connected to the top cover. The forward flexion control line fulcrum and the backward extension control line fulcrum are fixed to the base and arranged relative to a center of the angle control disk. The control line fixer is fixed to the top cover and arranged on a perpendicular bisector of a connecting line between the forward flexion control line fulcrum and the backward extension control line fulcrum.

Further, the forward flexion control line and the backward extension control line are arranged on side walls of two symmetrical sides of the bronchial blocking catheter, respectively. A front end of the forward flexion control line is connected to a side of the camera assembly, and a tail end of the forward flexion control line, after passing through the hollow rotating shaft of the angle control disk, bypasses the forward flexion control line fulcrum to be connected to the control line fixer. A front end of the backward extension control line is connected to an other side of the camera assembly, and a tail end of the backward extension control line, after passing through the hollow rotating shaft of the angle control disk, bypasses the backward extension control line fulcrum to be connected to the control line fixer.

Further, a hard outer envelope is arranged on an outer side of the stiff main catheter section, and the hard outer envelope is made of PVC (poly vinyl chloride).

Further, a front end of the camera video line is connected to the camera assembly, and a tail end of the camera video line is connected to a video display.

Further, a tail end of the ventilation lumen passes through an outer opening of the ventilation lumen at a tail end of the control handle, and is connected to a pressure safety valve and an oxygen connecting port.

Further, light sources and a camera are arranged on the front end face of the camera assembly.

The present disclosure has the beneficial effects that:

The present disclosure provides a disposable angle-adjustable visual bronchial blocker, a bronchus to be entered can be accurately determined by using the front-facing camera assembly, and the forward flexion control line and the backward extension control line can then be pulled by using the angle control disk, such that the soft flexible section can be flexed forward or extended backward according to requirements, thereby effectively meeting a requirement that the bronchial blocker needs to be adjusted in a direction from side to side in order to enter the bronchus on either side. After entering the designated bronchus, the inflatable air bag is started to complete the blocking operation, and the clinical operation efficiency is effectively improved because there using the fiberoptic bronchoscope for guidance is no needed.

Figure 1:
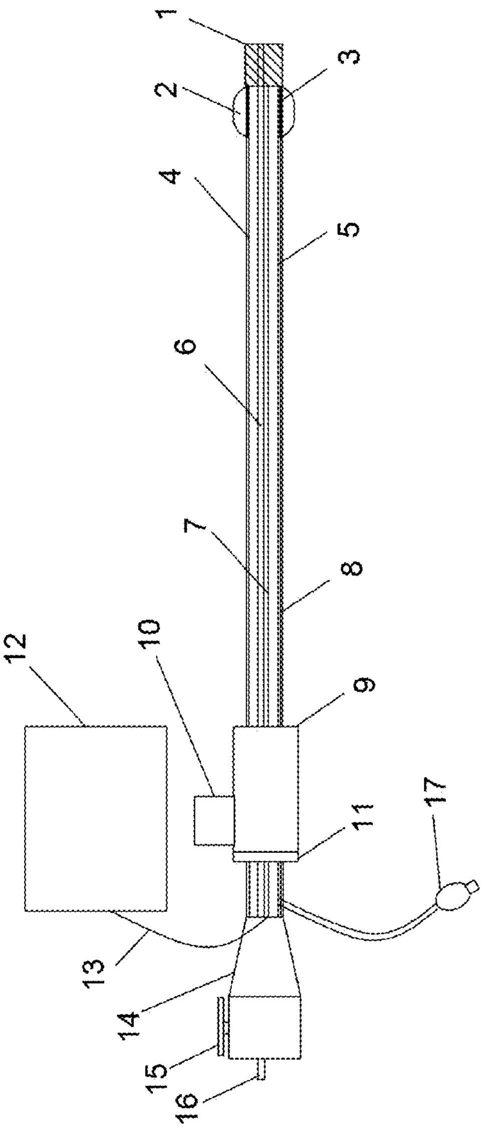
FIG. 1 is a structural diagram of a disposable angle-adjustable visual bronchial blocker.

In the drawings: 1—camera assembly; 2—inflatable air bag; 3—soft flexible section; 4—forward flexion control line; 5—backward extension control line; 6—ventilation lumen; 7—stiff main catheter section; 8—hard outer envelope; 9—endotracheal tube connecting port; 10—breathing circuit connecting port; 11—closeable spiral port; 12—video display; 13—video connection line; 14—control handle; 15—angle control disk; 16—outer opening of ventilation lumen; 17—inflating port; 18—hollow rotating shaft; 19—forward flexion control line fulcrum; 20—backward extension control line fulcrum; 21—control line fixer; 22—camera; 23—light source; 24—pressure safety valve; 25—oxygen connecting port.

Like reference numerals in the drawings represent like parts.

DETAILED DESCRIPTION OF THE EMBODIMENTS

The present disclosure is further described below with reference to specific embodiments. It should be understood that these embodiments are merely used to illustrate the present disclosure rather than limiting the scope of the present disclosure. In addition, it should be understood that after reading the teaching of the present disclosure, those skilled in the art can make various changes or modifications to the present disclosure, and these equivalent forms also fall within the scope defined by the appended claims of the present disclosure.

As shown in FIG. 1, the present disclosure relates to a disposable angle-adjustable visual bronchial blocker, including a bronchial blocking catheter. The bronchial blocking catheter includes a stiff main catheter section 7 and a soft flexible section 3. Although hardness of the stiff main catheter section 7 is higher than hardness of the soft flexible section, the stiff main catheter section 7 can still be bent to a certain extent, thus keeping the shape and protecting interior lines while passing through the endotracheal tube. An inflatable air bag 2 is arranged on an outer side of the flexible section, a camera assembly 1 is arranged at a front end of the flexible section. An interior of the bronchial blocking catheter comprises a forward flexion control line 4, a backward extension control line 5, a ventilation lumen 6, an inflation line and a camera video line which are arranged in parallel in a direction of the bronchial blocking catheter. A control handle 14 is arranged at a tail end of the bronchial blocking catheter, and an angle control disk 15 for controlling a degree of bending of the soft flexible section 2 is arranged on a side face of the control handle 14. A front opening of the ventilation lumen 6 is formed in a front end face of the camera assembly 1, such that secretions in an airway can be sucked through the ventilation lumen 6.

Figure 2:
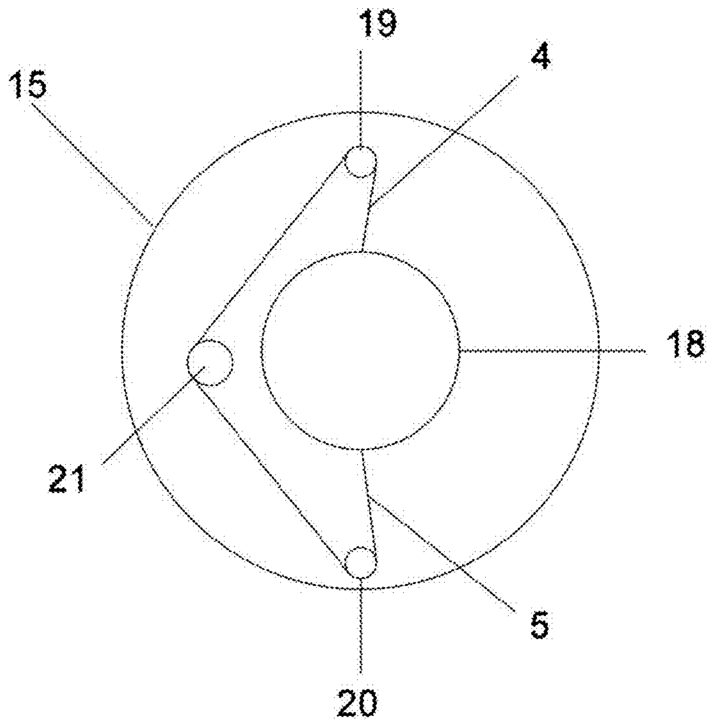
FIG. 2 is a cross-sectional diagram of an angle control disk in FIG. 1.

As shown in FIG. 2, an interior of the angle control disk 15 includes a base, a top cover, a hollow rotating shaft, a forward flexion control line fulcrum 19, a backward extension control line fulcrum 20 and a control line fixer 21. The base is fixedly connected to the control handle 14, the hollow rotating shaft 18 and the angle control disk 15 are concentric, an end of the hollow rotating shaft 18 is rotatably connected to the control handle 14, and another end of the hollow rotating shaft 18 is connected to the top cover. The forward flexion control line fulcrum 19 and the backward extension control line fulcrum 20 are fixed to the base and arranged relative to a center of the angle control disk 15. The control line fixer 21 is fixed to the top cover and arranged on a perpendicular bisector of a connecting line between the forward flexion control line fulcrum 19 and the backward extension control line fulcrum 20.

The forward flexion control line 4 and the backward extension control line 5 are arranged on side walls of two symmetrical sides of the bronchial blocking catheter, respectively. A front end of the forward flexion control line 4 is connected to a side of the camera assembly 1, and a tail end of the forward flexion control line 4, after passing through the hollow rotating shaft 18 of the angle control disk 15, bypasses the forward flexion control line fulcrum 19 to be connected to the control line fixer 21. A front end of the backward extension control line 5 is connected to an other side of the camera assembly 1, and a tail end of the backward extension control line 5, after passing through the hollow rotating shaft 18 of the angle control disk 15, bypasses the backward extension control line fulcrum 20 to be connected to the control line fixer 21.

Specifically, during use, the top cover of the angle control disk 15 can be rotated, and the top cover drives the control line fixer 21 to rotate around the hollow rotating shaft 18. If the top cover drives the control line fixer 21 to rotate counterclockwise, the forward flexion control line 4 is tightened while the backward extension control line 5 is loosened, such that the soft flexible section 3 of the bronchial blocking catheter can bend towards a forward flexion direction. Meanwhile, the camera assembly 1 rotates in the same direction, such that condition ahead can be seen clearly, and whether the bronchus is the one needing to be blocked is determined. Similarly, if the soft flexible section 3 needs to bend towards a backward extension direction, the top cover drives the control line fixer 21 to rotate clockwise. A rotation angle and a length of pulling can be specifically designed according to actual situation, the rotation angle is usually about 180°. After a forward direction is confirmed, the bronchial blocker of the present disclosure is pushed into the bronchus to be blocked, then air is supplied through an inflating port 17, and the inflatable air bag 2 is started to complete blocking. As the front end camera assembly 1 is relatively closer to the inflatable air bag 2, a situation that the front end camera assembly enters lobar bronchus due to the blocker is too long is avoided, and influence of operation range during lung resection is avoided.

Further, a hard outer envelope 8 is arranged on an outer side of the stiff main catheter section 7, and the hard outer envelope 8 is made of PVC.

Further, a front end of the camera video line is connected to the camera assembly 1, and a tail end of the camera video line is connected to a video display 12 through a video connecting line 13.

Figure 3:
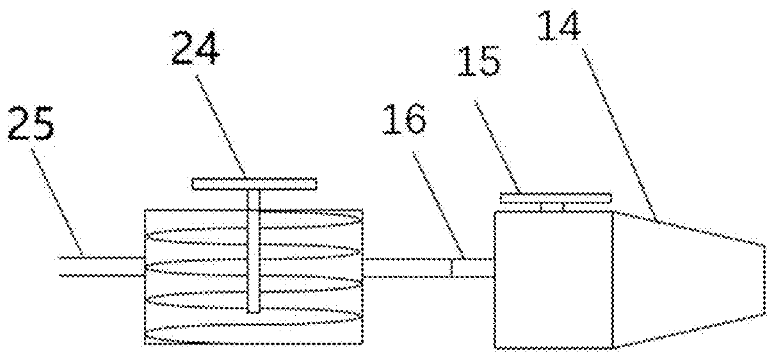
FIG. 3 is a connection diagram of a tail end of a control handle in FIG. 1.

Further, as shown in FIG. 3, a tail end of the ventilation lumen 6 passes through an outer opening 16 of the ventilation lumen at a tail end of the control handle 14, and is connected to a pressure safety valve 24 and an oxygen connecting port 25, such that oxygen can be continuously delivered to the lung in the operative side during the operation. Moreover, a certain continuous airway pressure is set to alleviate hypoxia caused by single-lung ventilation.

Figure 4:
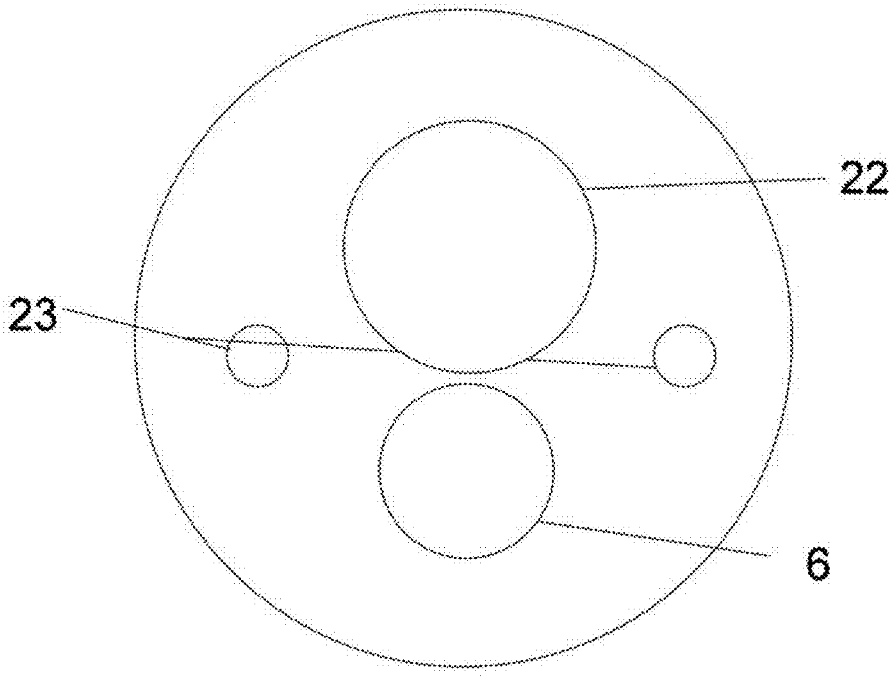
FIG. 4 is a schematic diagram of a head end of a camera assembly in FIG. 1.

Further, as shown in FIG. 4, light sources 23 and a camera 22 are arranged on the front end face of the camera assembly 1. The light sources 23 are symmetrically arranged on both sides of the camera 22 and the ventilation lumen 6. Preferably, the light sources 23 are LED (light-emitting diode) light sources.

It should be emphasized that the length and diameter of the bronchial blocker are not limited by the schematic proportion of the schematic diagram, and can be adjusted according to the actual use situation.

What is claimed is:

1. A disposable angle-adjustable visual bronchial blocker, comprising a bronchial blocking catheter, wherein the bronchial blocking catheter comprises a stiff main catheter section (7), and a soft flexible section (3); an inflatable air bag (2) is arranged at an outer side of the flexible section, a camera assembly (1) is arranged at a front end of the flexible section; an interior of the bronchial blocking catheter comprises a forward flexion control line (4), a backward extension control line (5), a ventilation lumen (6), an inflation line and a camera video line, and the forward flexion control line (4), the backward extension control line (5), the ventilation lumen (6), the inflation line and the camera video line are arranged in parallel in a direction of the bronchial blocking catheter; a control handle (14) is arranged at a tail end of the bronchial blocking catheter, and an angle control disk (15) for controlling a degree of bending of the soft flexible section (3) is arranged at a side face of the control handle (14); and a front opening of the ventilation lumen (6) is formed in a front end face of the camera assembly (1).

2. The disposable angle-adjustable visual bronchial blocker according to claim 1, wherein an interior of the angle control disk (15) comprises a base, a top cover, a hollow rotating shaft (18), a forward flexion control line fulcrum (19), a backward extension control line fulcrum (20) and a control line fixer (21); the base is fixedly connected to the control handle (14); the hollow rotating shaft (18) and the angle control disk (15) are concentric; an end of the hollow rotating shaft (18) is rotatably connected to the control handle (14), and another end of the hollow rotating shaft (18) is connected to the top cover; the forward flexion control line fulcrum (19) and the backward extension control line fulcrum (20) are fixed to the base and arranged relative to a center of the angle control disk (15); the control line fixer (21) is fixed to the top cover and arranged on a perpendicular bisector of a connecting line between the forward flexion control line fulcrum (19) and the backward extension control line fulcrum (20).

3. The disposable angle-adjustable visual bronchial blocker according to claim 2, wherein the forward flexion control line (4) and the backward extension control line (5) are arranged on side walls of two symmetrical sides of the bronchial blocking catheter, respectively; a front end of the forward flexion control line (4) is connected to a side of the camera assembly (1), and a tail end of the forward flexion control line (4), after passing through the hollow rotating shaft (18) of the angle control disk (15), bypasses the forward flexion control line fulcrum (19) to be connected to the control line fixer (21); and a front end of the backward extension control line (5) is connected to an other side of the camera assembly (1), and a tail end of the backward extension control line (5), after passing through the hollow rotating shaft (18) of the angle control disk (15), bypasses the backward extension control line fulcrum (20) to be connected to the control line fixer (21).

4. The disposable angle-adjustable visual bronchial blocker according to claim 1, wherein a hard outer envelope (8) is arranged on an outer side of the stiff main catheter section (7), and the hard outer envelope (8) is made of poly vinyl chloride (PVC).

5. The disposable angle-adjustable visual bronchial blocker according to claim 1, wherein a front end of the camera video line is connected to the camera assembly (1), and a tail end of the camera video line is connected to a video display (12).

6. The disposable angle-adjustable visual bronchial blocker according to claim 1, wherein a tail end of the ventilation lumen (6) passes through an outer opening (16) of the ventilation lumen at a tail end of the control handle (14), and is connected to a pressure safety valve (24) and an oxygen connecting port (25).

7. The disposable angle-adjustable visual bronchial blocker according to claim 1, wherein light sources (23) and a camera (22) are arranged on the front end face of the camera assembly (1).

* * * * *